United States Patent [19]

Farrar et al.

[11] Patent Number: 5,210,324
[45] Date of Patent: May 11, 1993

[54] MONOMER PRODUCTION

[75] Inventors: David Farrar; Malcolm Hawe, both of West Yorkshire, England

[73] Assignee: Allied Colloids Limited, England

[21] Appl. No.: 421,304

[22] Filed: Oct. 11, 1989

Related U.S. Application Data

[63] Continuation of Ser. No. 308,956, Feb. 6, 1989, abandoned, which is a continuation of Ser. No. 117,365, Oct. 28, 1987, abandoned, which is a continuation of Ser. No. 894,352, Aug. 7, 1986, abandoned.

[30] Foreign Application Priority Data

Aug. 12, 1985 [GB] United Kingdom ............... 8520218
Feb. 14, 1986 [GB] United Kingdom ............... 8603656

[51] Int. Cl.$^5$ ................... C07C 43/11; C07C 43/18; C07C 43/20
[52] U.S. Cl. ................... 568/616; 568/673; 568/675; 568/687; 568/689
[58] Field of Search ............... 568/616, 675, 673, 687, 568/689

[56] References Cited

U.S. PATENT DOCUMENTS 2,201,074  5/1940  Britton et al. ................... 568/616
4,142,042  2/1979  Goble .

FOREIGN PATENT DOCUMENTS 66179   12/1982  European Pat. Off. ............ 568/616
1120963  7/1956  France .
108205   8/1975  Japan ................................ 568/616

Primary Examiner—José Dees
Assistant Examiner—Joseph M. Conrad, III
Attorney, Agent, or Firm—Andrus, Sceales, Starke & Sawall

[57] ABSTRACT

A new process for producing allyl ethers, usually $C_{8-30}$ alkyl $(CH_2CH_2O)_{5-100}$ allyl ether, by forming a solution of an alcohol, usually a surfactant alcohol, in a solvent capable of forming an azeotrope with water, azeotroping the mixture to remove substantially all the water, adding an alkalimetal alkoxide, usually sodium methoxide, removing the alkanol formed, usually by azeotroping with the solvent, adding a halide, usually allyl chloride, and recovering the allyl ether. The ethers are useful as monomers, for example to produce polymers by copolymerising with copolymerisable ethylenically unsaturated comonomers for a wide range of applications.

10 Claims, No Drawings

MONOMER PRODUCTION

This application is a continuation of copending application Ser. No. 07/308,956 filed Feb. 6, 1989, now abandoned, which in turn is a continuation of copending application Ser. No. 07/117,365 filed Oct. 28, 1987, now abandoned, which in turn is a continuation of copending application Ser. No. 06/894,352 filed Aug. 7, 1986, now abandoned.

The present invention relates to a new synthetic process for producing (meth) allyl ethers useful, in particular, as monomers in the production of polymers such as are disclosed in EP0172025 and EP0172723.

It is known to produce alkyl ethers by the Williamson synthesis in which a metal alkoxide is reacted with an alkyl halide or with dialkyl sulphate. The process has been used to produce allyl ethers. A metal alkoxide is generally produced by the reaction of the anhydrous alcohol with an alkalimetal or an alkalimetal hydroxide or hydride. For instance, in GB 1273552 it is stated that an allyl ether of a polyalkyleneoxy compound may be synthesised by reacting the compound with allyl chloride in the presence of sodium or potassium hydroxide or metallic sodium.

One problem with the prior art processes is that the reaction of an alkali metal with an alcohol can be dangerous, in particular because of the production of hydrogen gas in the reaction, and difficult to control. Another problem is that reaction is not suitable for many alcohols and the conventional Williamson synthesis is unsatisfactory for many starting materials. For instance, we have tried to use the process when the alcohol is an ethoxylate of stearyl alcohol, but have found that there is little reaction of sodium metal even when the alcohol is molten and shearing is applied to the reaction mixture, such a reaction being dangerous as well as inefficient. When the reaction product is reacted with allyl chloride the yield of the desired allyl ether is very low and the product mixture contains a large number of products of undesirable side reactions. Another problem with prior art processes is that when the reaction is carried out in the presence of an alkali metal hydroxide very low yields are obtained.

Another problem is that it is particularly difficult to obtain good yields when the ether contains a polyalkoxy chain. Finally, a serious difficulty with the production of allyl ether compounds is that the degree of conversion to the desired ether is difficult or impossible to assess without polymerising the product and testing the polymer to check the presence of side-chains derived from the desired allyl ether product.

According to the invention a process of making a compound of the formula I $$CH_2=CR^2CH_2OX_yR^1 \qquad I$$

in which
X is alkyleneoxy, preferably ethylenoxy, propyleneoxy and/or butyleneoxy, and y is 0 or an integer;
$R^1$ is R or $CH_2CR^2=CH_2$;
R is H, a lower alkyl group or a hydrophobic group containing at least 8 carbon atoms;
$R^2$ is hydrogen or methyl, comprises mixing an alcohol of the formula II,

HOE \qquad II in which
E is one of $X_yR^1$ and $CH_2CR^2=CH_2$; with a solvent which is capable of forming an azetrope with water, dehydrating the mixture by azeotropic distillation until it is substantially anhydrous, adding an alkali metal alkoxide $MOR^3$, in which $R^3$ is $C_{1-6}$ alkyl and M is an alkali metal, to form the alkali metal alcoholate MOE and an alcohol $R^3OH$, removing substantially all the alcohol by distillation and then reacting the alcoholate with a halide of the formula III,

FY in which Y is halogen and F is the other of $X_yR^1$ and $CH_2CR^2=CH_2$.

In the process it is most convenient for the alcohol HOE to be $HOX_yR^1$ and for $R^1$ to be R. Thus the halide is generally a (meth) allyl halide $CH_2=CR^2-CH_2Y$ in which Y is a halogen preferably chlorine but may also be fluorine or bromine.

In the process it is necessary to include the initial dehydration step to remove substantially all the water. Water may be present in the starting material, especially in a compound $HOX_yR^1$, or in the reaction vessel. Preferably the amount of water in the reaction mixture is less than 0.5 or more preferably 0.1 and ideally less than 0.05% by weight. We believe that water in the reaction mixture may react with other components of the reaction mixture to give undesirable by-products. For example water may react with the alkali metal alkoxide to form the hydroxide and the etherification reaction would not proceed. Alternatively water may react with the halide FY to give the alcohol which would not react in the etherification step; because of the relatively high molecular weight of the compound HOE especially when E is $X_yR$ even a small amount of water would render much of the starting material inactive.

Although it might be considered possible to remove water from the starting material, by using chemical dehydrating agents, we have found that this is not practical. To enable the water to be removed under conditions which are not such as to form other impurities, it has been found that the water must be removed by azeotropic distillation. It is preferred that the temperature in the reaction vessel is maintained below 150° C., preferably below 130° C. or 120° C. throughout the process, to reduce side-reactions.

In the new process the solvent is capable of forming an azeotrope with water, and conveniently also with the alcohol $R^3OH$. If the solvent is capable of forming an azeotrope with $R^3OH$ it is possible and advantageous to remove that alcohol from the reaction mixture before addition of the halide by azeotropic distillation. If the solvent is not capable of forming an azeotrope with $R^3OH$ then it must have a higher boiling point than $R^3OH$ in order that the alcohol may be removed the reaction mixture by distillation ahead of the solvent. However it is preferred for the solvent to have a boiling point of less than 150° C., preferably less than 130° C. or 120° C. in order that the solvent may be removed from the final product mixture at a temperature at which the allyl ether does not polymerise.

If $R^3OH$ is not substantially entirely removed from the reaction mixture before addition of FY then poor yields of the desired product are obtained.

The solvent may also act to remove volatile by-products or unreacted starting materials from the product mixture.

The solvent is unreactive in the reaction mixture. The solvent may be non-polar; for best results, however, it is preferred that the solvent has some degree of polarity, for example, a polarity Eo of up to 0.5 preferably up to 0.3 on the Hildebrand scale although it should be substantially immiscible with water. The solvent is preferably selected from hexane, cyclohexane, heptane, petroleum ether fractions, benzene, xylene and toluene. It is economic to recycle the solvent distilled over during or at the end of the process and so it is advantageous for the solvent to consist of a single component. The preferred solvent is toluene.

In conventional Williamson syntheses the reaction mixtures are homogeneous, any solid reactants being soluble in the liquid reactants or in their carrier solvents. Thus, for example in a reaction using sodium methoxide in methanol reacting initially with benzyl alcohol, the sodium methoxide is freely soluble in the benzyl alcohol/methanol mixture. There has thus never been any need for the inclusion of other solvents. Although it is not expected that alkali metalalkoxides would be insufficiently soluble in a mixture of the corresponding alcohol, used as a carrier solvent, and the alcohol of the formula II, we have found that compounds of the formula II will not react to a sufficient degree with sodium alkoxide in the absence of a solvent of the specified type.

At the end of the reaction the solvent is generally removed from the product allyl ether. It may be removed by evaporation, and it is generally found convenient to lower the temperature at which it may be removed to minimise breakdown of the allyl ether product. This may be done, for example by adding a cosolvent with which the solvent may form an azeotropic mixture and azeotroping the two solvents. A suitable cosolvent has been found to be water. Alternatively or additionally, the pressure above the product mixture is reduced to lower the temperature at which the solvent is removed. Although the alkali-metal halide may be removed from the allyl ether product if desired, it is often unnecessary to do so since it has little adverse effect on the product.

The alkali metal alkoxide may be a lower alkoxide, ie having from 1 to 6 carbon atoms, preferably the methoxide or ethoxide. The alkali metal is generally potassium or, preferably, sodium. The alkoxide is for example sodium ethoxide, most preferably sodium methoxide. The alkoxide is generally supplied in the form of a solution, for example in the corresponding alcohol. Thus sodium methoxide is generally supplied in the form of a solution in methanol. Any such solvent is substantially completely removed from the reaction mixture before addition of the halide FY, to minimise side reactions. Alcohols may be removed by evaporation, eg fractional distillation, or may form an azeotrope with the reaction solvent.

If one attempts to carry out the reaction using, e.g., sodium metal in place of alkali metal alkoxide (i.e., as in a conventional Williamson synthesis), the reaction proceeds slowly at first as the reaction mixture is inhomogeneous. To try to render the mixture homogeneous, for example by blending is extremely dangerous. The reaction is liable to produce hydrogen as a by-product which is very explosive. Hydrolysis of the halide or some other reaction that prevents the etherification reaction proceeding seems to occur if water is present to assist the formation of a homogeneous mixture.

If alkali metal hydroxide is used in place of the alkoxide (e.g., as suggested in GB 1,275,552) hydrolysis of the halide starting material or some other undesirable interfering side reaction seems to occur and prevents the etherisfication proceeding.

The alcohol of the formula II is generally $HOX_pR^1$ which is a more readily available starting material than a halide $R^1X_yY$.

$X_y$ may be a hydrophobic group, that is it may consist of propyleneoxy and/or butyleneoxy groups. Preferably, however it has some hydrophilic character, by including ethyleneoxy groups. Thus $X_y$ is preferably $A_mB_nA_p$ in which A is propyleneoxy or butyleneoxy, B is ethoxy, n is a positive integer, m and p are each 0 or a positive integer less than n. n is generally above 2, preferably above 5, often above 10, usually below 100 and frequently 10 or 15 to 30. m and p are each generally 0.

Such an alcohol may have a hydroxy group at each end of the chain (ie R is hydrogen), in which case the product may include a disubstituted product ie $R^1$ is $-CH_2CR^2=CH_2$. Preferably however, one end of a polyoxyalkylene chain is blocked by a group R which is a lower alkyl group, eg having 1–6 carbon atoms, such as ethyl or methyl.

$HOX_pR$ may be the alcohol of a compound in which R is a hydrophobic group having more than 8 carbon atoms, in which case n and m each represent 0. The group R is a hydrophobic group usually comprising 8–30 carbon atoms, preferably 10–24 and most preferably 12–18 carbon atoms. More preferably R may be selected from alkyl, for instance octyl, lauryl or stearyl, aralkyl such as 2-phenyl ethyl ($C_2H_4Ph$), aryl such as naphthyl, alkaryl such as alkyl phenyl, where in the alkyl group generally contains 6–12 carbon atoms, cycloalkyl, including polycyclic alkyl groups, or mixtures of one or more such groups. Preferred groups are alkyl and aralkyl groups.

The process of the invention is most suitable for producing derivatives in which y is a positive integer, $X_y$ most preferably representing $A_mB_nA_p$, preferably $B_n$, as described above and R represents a $C_{8-30}$ alkyl chain.

The compound of the formula III FY is generally $CH_2=CR^2-CH_2Y$. The allyl halide may be any one of the halides but is generally bromide or, most preferably, chloride.

The products of the invention are generally used as monomers in polymerisation reactions. They may be homopolymerised or, preferably, are copolymerised with other comonomers, generally ethylenically unsaturated comonomers generally free of hydrophobic side chains. The polymers may be made by any conventional polymerisation process.

The following example illustrates the invention.

EXAMPLE 710g of a 10 mole ethoxylate of stearyl alcohol and 355g xylene are placed in the reaction vessel and dehydrated by azeotroping. 54g sodium methoxide as a 30% solution in methanol is added and the temperature raised to reflux. The methanol produced is removed by distillation. When all the methanol has been removed the reaction mixture is cooled to 60° C. and 76.5g allyl chloride is added carefully. The mixture is then heated to 110° C. for one hour. After one hour the mixture is transferred to a rotary evaporator where the xylene is removed under 760 mm vacuum and 100° C. Once the xylene is removed the finished product is left to cool.

The example was repeated using a range of different solvents for the reaction components. The quality of the allyl ether monomer produced was assessed by polymerising with ethyl acrylate and methacrylic acid monomers in the presence of varying amounts of a mercapto chain transfer agent and testing the viscosity properties of the resultant polymer. By this means the presence of ethoxylated alkyl side chains in the polymer and of crosslinking due to undesirable by-products containing two or more ethylenically unsaturated groups could be detected. The monomer quality was rated on a scale of 0-10, 10 being very good.

The following table shows the results for each solvent.

TABLE

| Solvent | Monomer Quality |
|---|---|
| Toluene | 9 |
| Cyclohexane | 5 |
| Petroleum ether 60/80 | 5 |
| Petroleum ether 81/100 | 9 |
| Petroleum ether 100/120 | 9 |
| Heptane | 8 |
| Hexane | 7 |

We claim:

1. In a process of making a compound of the formula $CH_2=CR^2CH_2OX_yR^1$ in which X is alkyleneoxy and y is an integer of from 2 to 100 and R1 is selected from lower alkyl and hydrophobic groups containing 8 to 30 carbon atoms and R2 is selected from hydrogen and methyl by reaction of an alkali metal alcoholate MOE wherein M is an alkali metal and E is $X_yR^1$
   with a halide of the formula FY in which Y is a halogen and F is $CH_2CR^2=CH_2$
   in a non-reactive solvent
   the improvement consisting of
   (a) mixing an alcohol of the fomrula HOE, wherein E is as defined above, with a non-reactive solvent which has a boiling point of below 150° C. and has a polarity Eo of up to 0.5 on the Hildebrand scale,
   (b) dehydrating the mixture by azeotropic distillation until it is substantially anhydrous and contains below 0.1% water,
   (c) adding an alkali metal alkoxide $MOR^3$ in which M is as defined above and $R^3$ is C1-6 alkyl to form the said alklai metal alkylate MOE and an alcohol $R^3OH$ that either forms an azeotrope with the solvent or has a lower boiling point than the solvent,
   (d) substantially completely removing the said alcohol $R^3OH$ by distillation and
   (e) then reacting the said alcoholate MOE in the resultant solution with the said halide FY.

2. A process according to claim 1 in which X is ethyleneoxy.

3. A process according to claim 1 in which the alcohol $R^3OH$ forms an azeotrope with the said solvent and the said distillation in step (d) is by azeotropic distillation.

4. A process according to claim 1 in which the solvent is selected from hexane, cyclohexane, heptane, petroleum ether, benzene, toluene and xylene.

5. A process according to claim 1 in which the solvent is toluene.

6. A process according to claim 1 in which $MOR^3$ is sodium methoxide.

7. A process according to claim 1 conducted at a temperature below 130° C.

8. A process according to claim 1 in which the said solvent is separated from the product of formula 1 and is recycled in the process.

9. A process of making a compound of the formula $CH_2=CR^2CH_2O(C_2H_4O)_yR^1$ wherein y is an integer from 5 to 100, $R^1$ contains 8 to 30 carbon atoms and is selected from alkyl and alkaryl groups and $R^2$ is selected from hydrogen and methyl, the process comprising mixing an alcohol of the formula $HO(C_2H_4O)_yR^1$ wherein $R^1$ and y are as defined above with a non-reactive solvent having a boiling point of below 150° C. and a polarity Eo of below 0.5 on the Hilebrand scale and selected from hexane, cyclohexane, heptane, petroleum ether, benzene, toluene and xylene, dehydrating the resultant mixture by azeotropic distillation until it is substantially anhydrous and contains below 0.1% water, adding sodium methoxide to form the sodium alcoholate of the said alcohol and methanol, substantially completely removing the methanol by distillation, and reacting the resultant alcoholate with (meth) allyl chloride.

10. In a process of making a compound of the formula $CH_2=CR^2CH_2OX_yR^1$ in which X is ethyleneoxy and y is an integer of from 2 to 100 and $R^1$ contains 8 to 30 carbon atoms and is selected from alkyl and alkaryl groups by reaction of an alkali metal alcoholate MOE wherein M is an alkali metal and E is $Y_7R^1$
   with a halide of the formula FY in which Y is a halogen and F is $CH_2CR^2=CH_2$
   in a non-reactive solvent
   (a) mixing an alcohol of the formula HOE, wherein E is as defined above, with a non-reactive solvent which has a boiling point of below 150° C. and has a polarity EO of up to 0.5 on the Hildebrand scale,
   (b) dehydrating the mixture by azeotropic distillation until it is substantially anhydrous and contains below 0.1% water,
   (c) adding an alkali metal alkoxide $MOR^3$ in which M is as defined above and $R^3$ is C1-6 alkyl to form the said alkali metal alkyalte MOE and an alcohol $R^3OH$ that either forms an azeotrope with the solvent or has a lower boiling point than the solvent,
   (d) substantially completely removing the said alcohol $R^3OH$ by distillation and
   (e) then reacting the said alcoholate MOE in the resultant solution with the said halide FY.

* * * * *